(12) United States Patent
Paranhos-Baccala et al.

(10) Patent No.: US 7,381,817 B2
(45) Date of Patent: Jun. 3, 2008

(54) LTR REGION OF MSRV-1 AND THE PROTEINS IT ENCODES, AND PROBES AND METHODS FOR DETECTING MSRV-1 RETROVIRUS

(75) Inventors: Glaucia Paranhos-Baccala, Lyons (FR); Herve Perron, Lyons (FR); Florence Komurian-Pradel, D'Or (FR)

(73) Assignee: Bio Merieux, Marcy l'Etoile (FR)

( * ) Notice: Subject to any disclaimer, the term of this patent is extended or adjusted under 35 U.S.C. 154(b) by 540 days.

(21) Appl. No.: 10/637,565

(22) Filed: Aug. 11, 2003

(65) Prior Publication Data
US 2004/0043381 A1 Mar. 4, 2004

Related U.S. Application Data

(63) Continuation of application No. 09/890,340, filed as application No. PCT/IB00/00159 on Feb. 15, 2000, now abandoned.

(30) Foreign Application Priority Data
Feb. 15, 1999 (EP) ................................. 99420041

(51) Int. Cl.
*C07H 21/04* (2006.01)
*A61K 39/00* (2006.01)
(52) U.S. Cl. ................................. 536/23.72; 424/207.1
(58) Field of Classification Search ...................... None
See application file for complete search history.

(56) References Cited

U.S. PATENT DOCUMENTS

| | | | |
|---|---|---|---|
| 5,800,980 A | 9/1998 | Perron et al. | |
| 5,871,745 A | 2/1999 | Perron et al. | |
| 5,871,996 A | 2/1999 | Perron et al. | |
| 5,962,217 A | 10/1999 | Perron et al. | |
| 6,001,987 A | 12/1999 | Perron et al. | |
| 6,582,703 B2 * | 6/2003 | Perron et al. | 424/204.1 |

FOREIGN PATENT DOCUMENTS

| | | |
|---|---|---|
| FR | 2 737 500 A1 | 2/1997 |
| WO | WO 93/20188 A1 | 10/1993 |
| WO | WO 94/28138 A1 | 12/1994 |
| WO | WO 95/21256 A1 | 8/1995 |
| WO | WO 98/23755 A1 | 6/1998 |
| WO | WO 99/02666 A1 | 1/1999 |
| WO | WO 99/02696 A1 | 1/1999 |

OTHER PUBLICATIONS

R. Komurian-Pradel et al., "Molecular Cloning and Characterization Of MSRV-Related Sequences Associated with Retrovirus-Like Particles," Virology, 260, 1-9 (1999), pp. 1-9.

H. Perron et al., "Molecular Identification of a Novel Retrovirus Repeatedly Isolated from Patients with Multiple Sclerosis," by Proc. Natl. Acad. Sci USA, vol. 94, pp. 7583-7588, Jul. 1997.

T. Heinemeyer et al., "Databases on Transcriptional Regulation: TRANSFAC, TRRD and COMPEL," Nucleic Acids Research, 1998, vol. 26, No. 1, pp. 362-367.

H. Perron et al., "Herpes Simplex Virus ICP0 and ICP4 Immediate Early Proteins Strongly Enhance Expression of a Retrovirus Harboured by a Leptomeningeal Cell Line from a Patient with Multiple Sclerosis," Journal of General Virology, 1993, 74, pp. 65-72.

H. Perron et al., "Leptomeningeal Cell Line from Multiple Sclerosis with Reverse Transcriptase Activity and Viral Particles," Res. Virol., 1989, 140, pp. 551-561.

T. Maniatis et al., "Molecular Cloning", 1982, vol. 1, pp. 7.53-7.55.

H. Perron et al., "In Vitro Transmission and Antigenicity of a Retrovirus Isolated from a Multiple Sclerosis Patient," Res. Virol., 1992, 143, pp. 337-349.

Fujinami and Libbey, "Endogenous Retroviruses: Are They the Cause of Multiple Sclerosis?," Trends in Microbiology, Jul. 1999; vol. 7, No. 7, pp. 263-264.

Blond et al., "Molecular Characterization and Placental Expression of HERV-W, a New Human Endogenous Retrovirus Family," Journal of Virology, 1999, vol. 73, No. 2, pp. 1175-1185.

Sequence Alignment of SEQ ID No. 2 with SEQ ID No. 12 from WO 99/02666 of Ott et al., Accession No. AX001030; Submission date: Jan. 21, 1999 from GenEmbl database.

Pauley, Protein- Nucleic Acid Sequence alignment of Instant SEQ ID No. 2 with GenEmbl Database Accession No. AC000064; Entry date: Nov. 13, 1999.

Steiner et al., "Infection and the Etiology and Pathogenesis of Multiple Sclerosis," Current Neurology and Neuroscience Reports, 2001; vol. 1, pp. 271-276.

* cited by examiner

*Primary Examiner*—Bruce R. Campell
*Assistant Examiner*—Bao Qun Li
(74) *Attorney, Agent, or Firm*—Oliff & Berridge PLC

(57) ABSTRACT

The invention relates to: a nucleotide fragment of an MSRV-1 LTR-RU5 region, comprising a nucleotide sequence encoding the expression of a protein, wherein the protein comprises a peptide sequence selected from the group consisting of: SEQ ID NO: 2, SEQ ID NO: 3, and SEQ ID NO: 4; complementary nucleotide fragments; probes and primers that hybridize to the fragment; proteins encoded by the fragment; antibodies directed against the proteins encoded by the fragment; and processes for detecting the presence of MSRV-1 using a probe or an antibody of the invention.

4 Claims, 3 Drawing Sheets

FIG. 2

Figure 1:
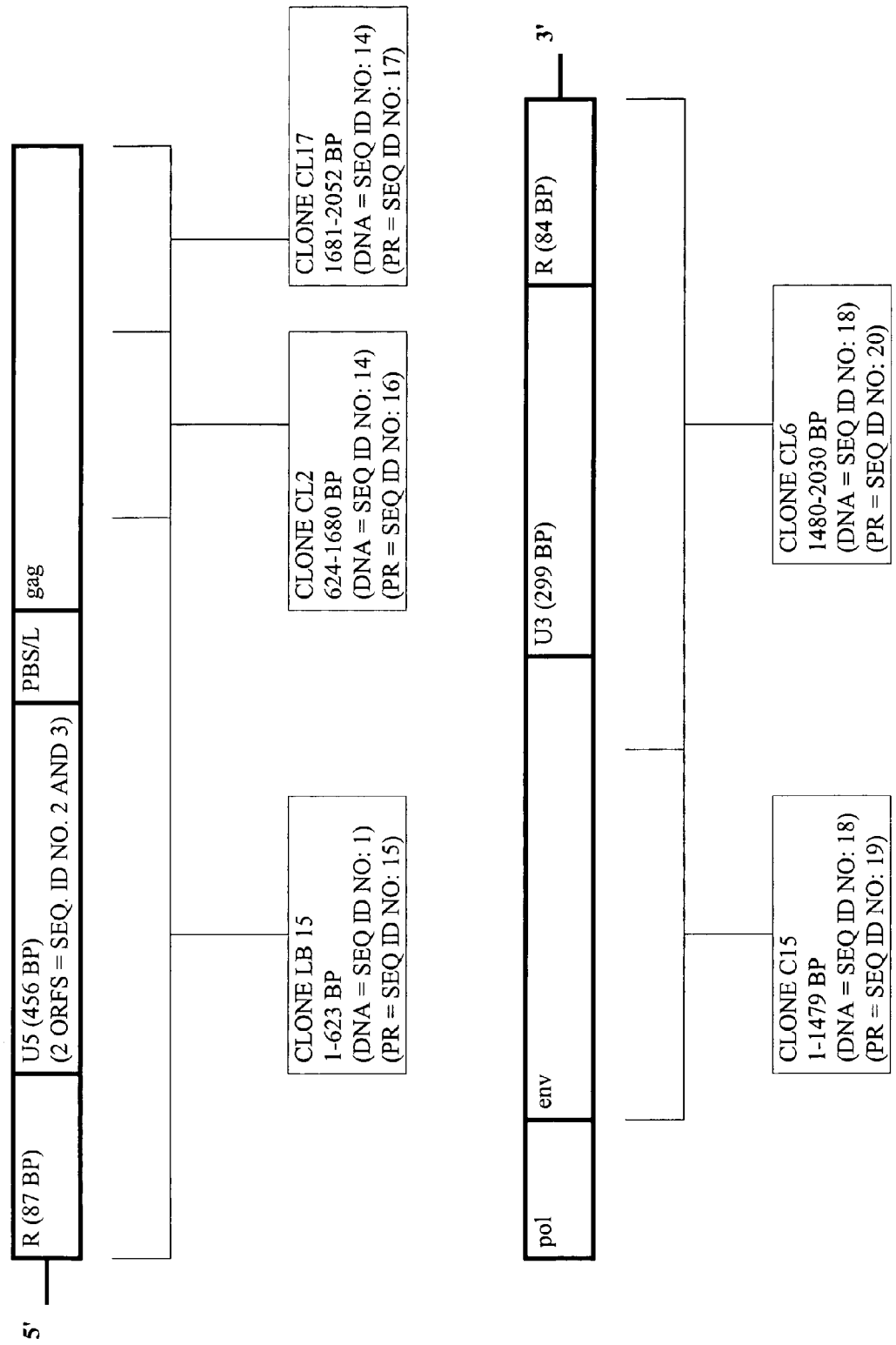

SEQUENCE LISTING

```
<160> NUMBER OF SEQ ID NOS: 20

<210> SEQ ID NO 1
<211> LENGTH: 1003
<212> TYPE: DNA
<213> ORGANISM: MSRV-1 retrovirus

<400> SEQUENCE: 1
cagcaacccc ctttgggtcc cctcccattg tatgggagct ctgttttcac tctatttcac      60
tctattaaat catgcaactg cactcttctg gtccgtgttt tttatggctc aagctgagct     120
tttgttcgcc atccaccact gctgtttgcc accgtcacag acccgctgct gacttccatc     180
cctttggatc cagcagagtg tccgctgtgc tcctgatcca gcacaggcgc ccattgcctc     240
tcccaattgg gctaaaggct tgccattgtt cctgcacagc taagtgcctg ggttcatcct     300
aatcgagctg aacactagtc actgggttcc acggttctct tccatgaccc atggcttcta     360
atagagctat aacactcact gcatggtcca agattccatt ccttggaatc cgtgagacca     420 agaacccag gtcagagaac acaaggcttg ccaccatgtt ggaagcagcc caccaccatt     480
ttggaagcag cccgccacta tcttgggagc tctgggagca aggaccccag gtaacaattt     540
ggtgaccacg aagggacctg aatccgcaac catgaaggga tctccaaagc aatgggaaac     600 gttcccccg aggcaaaaat gcccctagaa cgtattctgg agaattggga ccaatgtgac     660
actcagacgc taagaaagaa acgatttata ttcttctgca gtaccgcctg gccacaatat     720
cctcttcaag ggagagaaac ctggcttcct gagggaagta taaattataa catcatctta     780
cagctagacc tcttctgtag aaaggagggc aaatggagtg aagtgccata tgtgcaaact     840
ttcttttcat taagagacaa ctcacaatta tgtaaaaagt gtggtttatg ccctacagga     900
agccctcaga gtccacctcc ctaccccagc gtcccctccc cgactccttc ctcaactaat     960 aaggacccc ctttaaccca aacaccagtc caaaggaca tag                         1003

<210> SEQ ID NO 2
<211> LENGTH: 76
<212> TYPE: PRT
<213> ORGANISM: MSRV-1 retrovirus

<400> SEQUENCE: 2

Met Gln Leu His Ser Ser Gly Pro Cys Phe Leu Trp Leu Lys Leu Ser
1               5                   10                  15

Phe Cys Ser Pro Ser Thr Thr Ala Val Cys His Arg His Arg Pro Ala
            20                  25                  30

Ala Asp Phe His Pro Phe Gly Ser Ser Arg Val Ser Ala Val Leu Leu
        35                  40                  45
```

-continued

Ile Gln His Arg Arg Pro Leu Pro Leu Pro Ile Gly Leu Lys Ala Cys
    50                  55                  60

His Cys Ser Cys Thr Ala Lys Cys Leu Gly Ser Ser
65                  70                  75

<210> SEQ ID NO 3
<211> LENGTH: 64
<212> TYPE: PRT
<213> ORGANISM: MSRV-1 retrovirus

<400> SEQUENCE: 3

Met Ala Ser Asn Arg Ala Ile Thr Leu Thr Ala Trp Ser Lys Ile Pro
1               5                   10                  15

Phe Leu Gly Ile Arg Glu Thr Lys Asn Pro Arg Ser Glu Asn Thr Arg
                20                  25                  30

Leu Ala Thr Met Leu Glu Ala Ala His His His Phe Gly Ser Ser Pro
            35                  40                  45

Pro Leu Ser Trp Glu Leu Trp Glu Gln Gly Pro Gln Val Thr Ile Trp
    50                  55                  60

<210> SEQ ID NO 4
<211> LENGTH: 140
<212> TYPE: PRT
<213> ORGANISM: MSRV-1 retrovirus

<400> SEQUENCE: 4

Met Gln Leu His Ser Ser Gly Pro Cys Phe Leu Trp Leu Lys Leu Ser
1               5                   10                  15

Phe Cys Ser Pro Ser Thr Thr Ala Val Cys His Arg His Arg Pro Ala
                20                  25                  30

Ala Asp Phe His Pro Phe Gly Ser Ser Arg Val Ser Ala Val Leu Leu
            35                  40                  45

Ile Gln His Arg Arg Pro Leu Pro Leu Pro Ile Gly Leu Lys Ala Cys
    50                  55                  60

His Cys Ser Cys Thr Ala Lys Cys Leu Gly Ser Ser Met Ala Ser Asn
65                  70                  75                  80

Arg Ala Ile Thr Leu Thr Ala Trp Ser Lys Ile Pro Phe Leu Gly Ile
                85                  90                  95

Arg Glu Thr Lys Asn Pro Arg Ser Glu Asn Thr Arg Leu Ala Thr Met
            100                 105                 110

Leu Glu Ala Ala His His His Phe Gly Ser Ser Pro Pro Leu Ser Trp
        115                 120                 125

Glu Leu Trp Glu Gln Gly Pro Gln Val Thr Ile Trp
    130                 135                 140

<210> SEQ ID NO 5
<211> LENGTH: 8
<212> TYPE: DNA
<213> ORGANISM: MSRV-1 retrovirus
<220> FEATURE:
<221> NAME/KEY: polyA_site
<222> LOCATION: (1)..(8)

<400> SEQUENCE: 5 ygtgttyy                                                        8

<210> SEQ ID NO 6
<211> LENGTH: 6
<212> TYPE: DNA
<213> ORGANISM: MSRV-1 retrovirus

```
<220> FEATURE:
<221> NAME/KEY: TATA_signal
<222> LOCATION: (1)..(6)

<400> SEQUENCE: 6 tataaa                                                              6

<210> SEQ ID NO 7
<211> LENGTH: 6
<212> TYPE: DNA
<213> ORGANISM: MSRV-1 retrovirus
<220> FEATURE:
<221> NAME/KEY: polyA_signal
<222> LOCATION: (1)..(6)

<400> SEQUENCE: 7 aataaa                                                              6

<210> SEQ ID NO 8
<211> LENGTH: 22
<212> TYPE: DNA
<213> ORGANISM: Artificial Sequence
<220> FEATURE:
<223> OTHER INFORMATION: LB15 sense primer

<400> SEQUENCE: 8
gcaacagcaa cccccttttgg gt                                           22

<210> SEQ ID NO 9
<211> LENGTH: 25
<212> TYPE: DNA
<213> ORGANISM: Artificial Sequence
<220> FEATURE:
<223> OTHER INFORMATION: LB15 antisense primer

<400> SEQUENCE: 9
cttggagggt gcataaccag ggaat                                         25

<210> SEQ ID NO 10
<211> LENGTH: 28
<212> TYPE: DNA
<213> ORGANISM: Artificial Sequence
<220> FEATURE:
<223> OTHER INFORMATION: LB15 antisense primer

<400> SEQUENCE: 10
ctatgtcctt ttggactgct gtttgggt                                      28

<210> SEQ ID NO 11
<211> LENGTH: 30
<212> TYPE: DNA
<213> ORGANISM: Artificial Sequence
<220> FEATURE:
<223> OTHER INFORMATION: CL6 sense primer

<400> SEQUENCE: 11
gccatcaagc cacccaagaa ctcttaactt                                    30

<210> SEQ ID NO 12
<211> LENGTH: 30
<212> TYPE: DNA
<213> ORGANISM: Artificial Sequence
<220> FEATURE:
<223> OTHER INFORMATION: CL6 sense primer
```

<400> SEQUENCE: 12

```
ccaatagcca gaccattata tacactaatt                                   30
```

<210> SEQ ID NO 13
<211> LENGTH: 34
<212> TYPE: DNA
<213> ORGANISM: Artificial Sequence
<220> FEATURE:
<223> OTHER INFORMATION: CL6 antisense primer

<400> SEQUENCE: 13

```
gactcgctgc agatcgattt ttttttttt tttt                               34
```

<210> SEQ ID NO 14
<211> LENGTH: 2052
<212> TYPE: DNA
<213> ORGANISM: MSRV-1 retrovirus
<220> FEATURE:
<221> NAME/KEY: CDS
<222> LOCATION: (592)..(2049)

<400> SEQUENCE: 14

```
cagcaacccc ctttgggtcc cctcccattg tatgggagct ctgttttcac tctatttcac   60
tctattaaat catgcaactg cactcttctg gtccgtgttt tttatggctc aagctgagct   120
tttgttcgcc atccaccact gctgtttgcc accgtcacag accgctgct gacttccatc    180 cctttggatc cagcagagtg tccgctgtgc tcctgatcca gcacaggcgc ccattgcctc   240
tcccaattgg gctaaaggct tgccattgtt cctgcacagc taagtgcctg ggttcatcct   300
aatcgagctg aacactagtc actgggttcc acggttctct tccatgaccc atggcttcta   360
atagagctat aacactcact gcatggtcca agattccatt ccttggaatc cgtgagacca   420
agaaccccag gtcagagaac acaaggcttg ccaccatgtt ggaagcagcc caccaccatt   480
ttggaagcag cccgccacta tcttgggagc tctgggagca aggaccccag gtaacaattt   540
ggtgaccacg aagggacctg aatccgcaac catgaaggga tctccaaagc a atg gga   597
                                                        Met Gly
                                                         1 aac gtt ccc ccc gag gca aaa atg ccc cta gaa cgt att ctg gag aat   645
Asn Val Pro Pro Glu Ala Lys Met Pro Leu Glu Arg Ile Leu Glu Asn
          5                  10                  15 tgg gac caa tgt gac act cag acg cta aga aag aaa cga ttt ata ttc   693
Trp Asp Gln Cys Asp Thr Gln Thr Leu Arg Lys Lys Arg Phe Ile Phe
 20                  25                  30 ttc tgc agt acc gcc tgg cca caa tat cct ctt caa ggg aga gaa acc   741
Phe Cys Ser Thr Ala Trp Pro Gln Tyr Pro Leu Gln Gly Arg Glu Thr
 35                  40                  45                  50 tgg ctt cct gag gga agt ata aat tat aac atc atc tta cag cta gac   789
Trp Leu Pro Glu Gly Ser Ile Asn Tyr Asn Ile Ile Leu Gln Leu Asp
                 55                  60                  65 ctc ttc tgt aga aag gag ggc aaa tgg agt gaa gtg cca tat gtg caa   837
Leu Phe Cys Arg Lys Glu Gly Lys Trp Ser Glu Val Pro Tyr Val Gln
             70                  75                  80 act ttc ttt tca tta aga gac aac tca caa tta tgt aaa aag tgt ggt   885
Thr Phe Phe Ser Leu Arg Asp Asn Ser Gln Leu Cys Lys Lys Cys Gly
         85                  90                  95 tta tgc cct aca gga agc cct cag agt cca cct ccc tac ccc agc gtc   933
Leu Cys Pro Thr Gly Ser Pro Gln Ser Pro Pro Pro Tyr Pro Ser Val
    100                 105                 110
```

```
                                                                   -continued ccc tcc ccg act cct tcc tca act aat aag gac ccc cct tta acc caa       981
Pro Ser Pro Thr Pro Ser Ser Thr Asn Lys Asp Pro Pro Leu Thr Gln
115             120                 125                 130 acg gtc caa aag gag ata gac aaa ggg gta aac aat gaa cca aag agt      1029
Thr Val Gln Lys Glu Ile Asp Lys Gly Val Asn Asn Glu Pro Lys Ser
                135                 140                 145 gcc aat att ccc cga tta tgc ccc ctc caa gca gtg aga gga gga gaa      1077
Ala Asn Ile Pro Arg Leu Cys Pro Leu Gln Ala Val Arg Gly Gly Glu
            150                 155                 160 ttc ggc cca gcc aga gtg cct gta cct ttt tct ctc tca gac tta aag      1125
Phe Gly Pro Ala Arg Val Pro Val Pro Phe Ser Leu Ser Asp Leu Lys
        165                 170                 175 caa att aaa ata gac cta ggt aaa ttc tca gat aac cct gac ggc tat      1173
Gln Ile Lys Ile Asp Leu Gly Lys Phe Ser Asp Asn Pro Asp Gly Tyr
    180                 185                 190 att gat gtt tta caa ggg tta gga caa tcc ttt gat ctg aca tgg aga      1221
Ile Asp Val Leu Gln Gly Leu Gly Gln Ser Phe Asp Leu Thr Trp Arg
195                 200                 205                 210 gat ata atg tta cta cta aat cag aca cta acc cca aat gag aga agt      1269
Asp Ile Met Leu Leu Leu Asn Gln Thr Leu Thr Pro Asn Glu Arg Ser
                215                 220                 225 gcc gct gta act gca gcc cga gag ttt ggc gat ctt tgg tat ctc agt      1317
Ala Ala Val Thr Ala Ala Arg Glu Phe Gly Asp Leu Trp Tyr Leu Ser
                230                 235                 240 cag gcc aac aat agg atg aca aca gag gaa aga aca act ccc aca ggc      1365
Gln Ala Asn Asn Arg Met Thr Thr Glu Glu Arg Thr Thr Pro Thr Gly
            245                 250                 255 cag cag gca gtt ccc agt gta gac cct cat tgg gac aca gaa tca gaa      1413
Gln Gln Ala Val Pro Ser Val Asp Pro His Trp Asp Thr Glu Ser Glu
        260                 265                 270 cat gga gat tgg tgc cac aaa cat ttg cta act tgc gtg cta gaa gga      1461
His Gly Asp Trp Cys His Lys His Leu Leu Thr Cys Val Leu Glu Gly
275                 280                 285                 290 ctg agg aaa act agg aag aag cct atg aat tac tca atg atg tcc act      1509
Leu Arg Lys Thr Arg Lys Lys Pro Met Asn Tyr Ser Met Met Ser Thr
                295                 300                 305 ata aca cag gga aag gaa gaa aat ctt act gct ttt ctg gac aga cta      1557
Ile Thr Gln Gly Lys Glu Glu Asn Leu Thr Ala Phe Leu Asp Arg Leu
                310                 315                 320 agg gag gca ttg agg aag cat acc tcc ctg tca cct gac tct att gaa      1605
Arg Glu Ala Leu Arg Lys His Thr Ser Leu Ser Pro Asp Ser Ile Glu
        325                 330                 335 ggc caa cta atc tta aag gat aag ttt atc act cag tca gct gca gac      1653
Gly Gln Leu Ile Leu Lys Asp Lys Phe Ile Thr Gln Ser Ala Ala Asp
    340                 345                 350 att aga aaa aac ttc aaa agt ctg cct tta ggc tcg gaa caa aac tta      1701
Ile Arg Lys Asn Phe Lys Ser Leu Pro Leu Gly Ser Glu Gln Asn Leu
355                 360                 365                 370 gaa acc cta ttg aac ttg gca acc tcg gtt ttt tat aat aga gat cag      1749
Glu Thr Leu Leu Asn Leu Ala Thr Ser Val Phe Tyr Asn Arg Asp Gln
                375                 380                 385 gag gag cag gca gaa gga caa acg gga tta aaa aag aag gcc acc gct      1797
Glu Glu Gln Ala Glu Gly Gln Thr Gly Leu Lys Lys Lys Ala Thr Ala
                390                 395                 400 tta gtc atg gcc ctc agg caa gcg gac tat gga ggc tct gga aaa ggg      1845
Leu Val Met Ala Leu Arg Gln Ala Asp Tyr Gly Gly Ser Gly Lys Gly
        405                 410                 415 aaa agc tga gaa aat tgg atg cct aat agg gtt tgc ttc cag tgc ggt      1893
Lys Ser     Glu Asn Trp Met Pro Asn Arg Val Cys Phe Gln Cys Gly
420                 425                 430
```

```
cta caa gga cac ttt aaa aaa gat tgt cca agt aga aat aag ccg ccc     1941
Leu Gln Gly His Phe Lys Lys Asp Cys Pro Ser Arg Asn Lys Pro Pro
    435                 440                 445 cct tgt cca tgc ccc tta cgt caa ggg aat cac tgg aag gcc cac tgc     1989
Pro Cys Pro Cys Pro Leu Arg Gln Gly Asn His Trp Lys Ala His Cys
450                 455                 460                 465 ccc agg gga tga aga tac tct gag tca gaa gcc att aac cag atg atc     2037
Pro Arg Gly     Arg Tyr Ser Glu Ser Glu Ala Ile Asn Gln Met Ile
                    470                 475                 480 cag cag cag gac tga                                                  2052
Gln Gln Gln Asp
```

<210> SEQ ID NO 15
<211> LENGTH: 420
<212> TYPE: PRT
<213> ORGANISM: MSRV-1 retrovirus

<400> SEQUENCE: 15

```
Met Gly Asn Val Pro Pro Glu Ala Lys Met Pro Leu Glu Arg Ile Leu
1               5                   10                  15

Glu Asn Trp Asp Gln Cys Asp Thr Gln Thr Leu Arg Lys Lys Arg Phe
            20                  25                  30

Ile Phe Phe Cys Ser Thr Ala Trp Pro Gln Tyr Pro Leu Gln Gly Arg
        35                  40                  45

Glu Thr Trp Leu Pro Glu Gly Ser Ile Asn Tyr Asn Ile Ile Leu Gln
    50                  55                  60

Leu Asp Leu Phe Cys Arg Lys Glu Gly Lys Trp Ser Glu Val Pro Tyr
65                  70                  75                  80

Val Gln Thr Phe Phe Ser Leu Arg Asp Asn Ser Gln Leu Cys Lys Lys
                85                  90                  95

Cys Gly Leu Cys Pro Thr Gly Ser Pro Gln Ser Pro Pro Tyr Pro
            100                 105                 110

Ser Val Pro Ser Pro Thr Pro Ser Ser Thr Asn Lys Asp Pro Pro Leu
            115                 120                 125

Thr Gln Thr Val Gln Lys Glu Ile Asp Lys Gly Val Asn Asn Glu Pro
    130                 135                 140

Lys Ser Ala Asn Ile Pro Arg Leu Cys Pro Leu Gln Ala Val Arg Gly
145                 150                 155                 160

Gly Glu Phe Gly Pro Ala Arg Val Pro Val Pro Phe Ser Leu Ser Asp
                165                 170                 175

Leu Lys Gln Ile Lys Ile Asp Leu Gly Lys Phe Ser Asn Pro Asp
            180                 185                 190

Gly Tyr Ile Asp Val Leu Gln Gly Leu Gly Gln Ser Phe Asp Leu Thr
        195                 200                 205

Trp Arg Asp Ile Met Leu Leu Leu Asn Gln Thr Leu Thr Pro Asn Glu
    210                 215                 220

Arg Ser Ala Ala Val Thr Ala Ala Arg Glu Phe Gly Asp Leu Trp Tyr
225                 230                 235                 240

Leu Ser Gln Ala Asn Asn Arg Met Thr Thr Glu Glu Arg Thr Thr Pro
                245                 250                 255

Thr Gly Gln Gln Ala Val Pro Ser Val Asp Pro His Trp Asp Thr Glu
            260                 265                 270

Ser Glu His Gly Asp Trp Cys His Lys His Leu Leu Thr Cys Val Leu
        275                 280                 285

Glu Gly Leu Arg Lys Thr Arg Lys Lys Pro Met Asn Tyr Ser Met Met
    290                 295                 300
```

```
Ser Thr Ile Thr Gln Gly Lys Glu Glu Asn Leu Thr Ala Phe Leu Asp
305                 310                 315                 320

Arg Leu Arg Glu Ala Leu Arg Lys His Thr Ser Leu Ser Pro Asp Ser
                325                 330                 335

Ile Glu Gly Gln Leu Ile Leu Lys Asp Lys Phe Ile Thr Gln Ser Ala
            340                 345                 350

Ala Asp Ile Arg Lys Asn Phe Lys Ser Leu Pro Leu Gly Ser Glu Gln
        355                 360                 365

Asn Leu Glu Thr Leu Leu Asn Leu Ala Thr Ser Val Phe Tyr Asn Arg
    370                 375                 380

Asp Gln Glu Glu Gln Ala Glu Gly Gln Thr Gly Leu Lys Lys Lys Ala
385                 390                 395                 400

Thr Ala Leu Val Met Ala Leu Arg Gln Ala Asp Tyr Gly Gly Ser Gly
                405                 410                 415

Lys Gly Lys Ser
            420

<210> SEQ ID NO 16
<211> LENGTH: 48
<212> TYPE: PRT
<213> ORGANISM: MSRV-1 retrovirus

<400> SEQUENCE: 16

Glu Asn Trp Met Pro Asn Arg Val Cys Phe Gln Cys Gly Leu Gln Gly
1               5                   10                  15

His Phe Lys Lys Asp Cys Pro Ser Arg Asn Lys Pro Pro Cys Pro
            20                  25                  30

Cys Pro Leu Arg Gln Gly Asn His Trp Lys Ala His Cys Pro Arg Gly
        35                  40                  45

<210> SEQ ID NO 17
<211> LENGTH: 16
<212> TYPE: PRT
<213> ORGANISM: MSRV-1 retrovirus

<400> SEQUENCE: 17

Arg Tyr Ser Glu Ser Glu Ala Ile Asn Gln Met Ile Gln Gln Gln Asp
1               5                   10                  15

<210> SEQ ID NO 18
<211> LENGTH: 2030
<212> TYPE: DNA
<213> ORGANISM: MSRV-1 retrovirus
<220> FEATURE:
<221> NAME/KEY: CDS
<222> LOCATION: (1)..(1626)

<400> SEQUENCE: 18 atg gcc ctc cct tat cat act ttt ctc ttt act gtt ctc tta ccc cct    48
Met Ala Leu Pro Tyr His Thr Phe Leu Phe Thr Val Leu Leu Pro Pro
1               5                   10                  15 ttc gct ctc act gca ccc cct cca tgc tgc tgt aca acc agt agc tcc    96
Phe Ala Leu Thr Ala Pro Pro Pro Cys Cys Cys Thr Thr Ser Ser Ser
            20                  25                  30 cct tac caa gag ttt cta tga aga acg cgg ctt cct gga aat att gat   144
Pro Tyr Gln Glu Phe Leu     Arg Thr Arg Leu Pro Gly Asn Ile Asp
        35                      40                  45 gcc cca tca tat agg agt tta tct aag gga aac tcc acc ttc act gcc   192
Ala Pro Ser Tyr Arg Ser Leu Ser Lys Gly Asn Ser Thr Phe Thr Ala
    50                  55                  60
```

-continued

```
cac acc cat atg ccc cgc aac tgc tat aac tct gcc act ctt tgc atg        240
His Thr His Met Pro Arg Asn Cys Tyr Asn Ser Ala Thr Leu Cys Met
 65                  70                  75 cat gca aat act cat tat tgg aca ggg aaa atg att aat cct agt tgt        288
His Ala Asn Thr His Tyr Trp Thr Gly Lys Met Ile Asn Pro Ser Cys
 80                  85                  90                  95 cct gga gga ctt gga gcc act gtc tgt tgg act tac ttc acc cat acc        336
Pro Gly Gly Leu Gly Ala Thr Val Cys Trp Thr Tyr Phe Thr His Thr
                100                 105                 110 agt atg tct gat ggg ggt gga att caa ggt cag gca aga gaa aaa caa        384
Ser Met Ser Asp Gly Gly Gly Ile Gln Gly Gln Ala Arg Glu Lys Gln
            115                 120                 125 gta aag gaa gca atc tcc caa ctg acc cgg gga cat agc acc cct agc        432
Val Lys Glu Ala Ile Ser Gln Leu Thr Arg Gly His Ser Thr Pro Ser
        130                 135                 140 ccc tac aaa gga cta gtt ctc tca aaa cta cat gaa acc ctc cgt acc        480
Pro Tyr Lys Gly Leu Val Leu Ser Lys Leu His Glu Thr Leu Arg Thr
    145                 150                 155 cat act cgc ctg gtg agc cta ttt aat acc acc ctc act cgg ctc cat        528
His Thr Arg Leu Val Ser Leu Phe Asn Thr Thr Leu Thr Arg Leu His
160                 165                 170                 175 gag gtc tca gcc caa aac cct act aac tgt tgg atg tgc ctc ccc ctg        576
Glu Val Ser Ala Gln Asn Pro Thr Asn Cys Trp Met Cys Leu Pro Leu
                180                 185                 190 cac ttc agg cca tac att tca atc cct gtt cct gaa caa tgg aac aac        624
His Phe Arg Pro Tyr Ile Ser Ile Pro Val Pro Glu Gln Trp Asn Asn
            195                 200                 205 ttc agc aca gaa ata aac acc act tcc gtt tta gta gga cct ctt gtt        672
Phe Ser Thr Glu Ile Asn Thr Thr Ser Val Leu Val Gly Pro Leu Val
        210                 215                 220 tcc aat ctg gaa ata acc cat acc tca aac ctc acc tgt gta aaa ttt        720
Ser Asn Leu Glu Ile Thr His Thr Ser Asn Leu Thr Cys Val Lys Phe
    225                 230                 235 agc aat act ata gac aca acc agc tcc caa tgc atc agg tgg gta aca        768
Ser Asn Thr Ile Asp Thr Thr Ser Ser Gln Cys Ile Arg Trp Val Thr
240                 245                 250                 255 cct ccc aca cga ata gtc tgc cta ccc tca gga ata ttt ttt gtc tgt        816
Pro Pro Thr Arg Ile Val Cys Leu Pro Ser Gly Ile Phe Phe Val Cys
                260                 265                 270 ggt acc tca gcc tat cat tgt ttg aat ggc tct tca gaa tct atg tgc        864
Gly Thr Ser Ala Tyr His Cys Leu Asn Gly Ser Ser Glu Ser Met Cys
            275                 280                 285 ttc ctc tca ttc tta gtg ccc cct atg acc atc tac act gaa caa gat        912
Phe Leu Ser Phe Leu Val Pro Pro Met Thr Ile Tyr Thr Glu Gln Asp
        290                 295                 300 tta tac aat cat gtc gta cct aag ccc cac aac aaa aga gta ccc att        960
Leu Tyr Asn His Val Val Pro Lys Pro His Asn Lys Arg Val Pro Ile
    305                 310                 315 ctt cct ttt gtt atc aga gca gga gtg cta ggc aga cta ggt act ggc       1008
Leu Pro Phe Val Ile Arg Ala Gly Val Leu Gly Arg Leu Gly Thr Gly
320                 325                 330                 335 att ggc agt atc aca acc tct act cag ttc tac tac aaa cta tct caa       1056
Ile Gly Ser Ile Thr Thr Ser Thr Gln Phe Tyr Tyr Lys Leu Ser Gln
                340                 345                 350 gaa ata aat ggt gac atg gaa cag gtc act gac tcc ctg gtc acc ttg       1104
Glu Ile Asn Gly Asp Met Glu Gln Val Thr Asp Ser Leu Val Thr Leu
            355                 360                 365 caa gat caa ctt aac tcc cta gca gca gta gtc ctt caa aat cga aga       1152
Gln Asp Gln Leu Asn Ser Leu Ala Ala Val Val Leu Gln Asn Arg Arg
        370                 375                 380
```

-continued

```
gct tta gac ttg cta acc gcc aaa aga ggg gga acc tgt tta ttt tta      1200
Ala Leu Asp Leu Leu Thr Ala Lys Arg Gly Gly Thr Cys Leu Phe Leu
    385                 390                 395 gga gaa gaa cgc tgt tat tat gtt aat caa tcc aga att gtc act gag      1248
Gly Glu Glu Arg Cys Tyr Tyr Val Asn Gln Ser Arg Ile Val Thr Glu
400                 405                 410                 415 aaa gtt aaa gaa att cga gat cga ata caa tgt aga gca gag gag ctt      1296
Lys Val Lys Glu Ile Arg Asp Arg Ile Gln Cys Arg Ala Glu Glu Leu
                420                 425                 430 caa aac acc gaa cgc tgg ggc ctc ctc agc caa tgg atg ccc tgg gtt      1344
Gln Asn Thr Glu Arg Trp Gly Leu Leu Ser Gln Trp Met Pro Trp Val
            435                 440                 445 ctc ccc ttc tta gga cct cta gca gct cta ata ttg tta ctc ctc ttt      1392
Leu Pro Phe Leu Gly Pro Leu Ala Ala Leu Ile Leu Leu Leu Leu Phe
        450                 455                 460 gga ccc tgt atc ttt aac ctc ctt gtt aag ttt gtc tct tcc aga att      1440
Gly Pro Cys Ile Phe Asn Leu Leu Val Lys Phe Val Ser Ser Arg Ile
    465                 470                 475 gaa gct gta aag cta cag atg gtc tta caa atg gaa ccc cag atg gag      1488
Glu Ala Val Lys Leu Gln Met Val Leu Gln Met Glu Pro Gln Met Glu
480                 485                 490                 495 tcc atg act aag atc cac cgt gga ccc ctg gac cgg cct gct agc cca      1536
Ser Met Thr Lys Ile His Arg Gly Pro Leu Asp Arg Pro Ala Ser Pro
                500                 505                 510 tgc tcc gat gtt aat gac att gaa ggc acc cct ccc gag gaa atc tca      1584
Cys Ser Asp Val Asn Asp Ile Glu Gly Thr Pro Pro Glu Glu Ile Ser
            515                 520                 525 act gca caa ccc cta cta tgc ccc aat tca gcg gga agc agt              1626
Thr Ala Gln Pro Leu Leu Cys Pro Asn Ser Ala Gly Ser Ser
        530                 535                 540 tagagcggtc atcagccaac ctccccaaca gcacttgggt tttcctgttg agagggggga   1686
ctgagagaca ggactagctg gatttcctag gccaacgaag aatccctaag cctagctggg   1746
aaggtgactg catccacctc taaacatggg gcttgcaact tagctcacac ccgaccaatc   1806
agagagctca ctaaaatgct aattaggcaa aaataggagg taaagaaata gccaatcatc   1866
tattgcctga gagcacagcg ggagggacaa ggatcgggat ataaacccag gcattcgagc   1926
cggcaacggc aaccccccttt gggtcccctc cctttgtatg ggcgctctgt tttcactcta   1986
tttcactcta ttaaatcttg caactgaaaa aaaaaaaaaa aaaa                    2030

<210> SEQ ID NO 19
<211> LENGTH: 38
<212> TYPE: PRT
<213> ORGANISM: MSRV-1 retrovirus

<400> SEQUENCE: 19

Met Ala Leu Pro Tyr His Thr Phe Leu Phe Thr Val Leu Leu Pro Pro
1               5                   10                  15

Phe Ala Leu Thr Ala Pro Pro Pro Cys Cys Cys Thr Thr Ser Ser Ser
            20                  25                  30

Pro Tyr Gln Glu Phe Leu
        35

<210> SEQ ID NO 20
<211> LENGTH: 503
<212> TYPE: PRT
<213> ORGANISM: MSRV-1 retrovirus
```

<400> SEQUENCE: 20

```
Arg Thr Arg Leu Pro Gly Asn Ile Asp Ala Pro Ser Tyr Arg Ser Leu
1               5                   10                  15
Ser Lys Gly Asn Ser Thr Phe Thr Ala His Thr His Met Pro Arg Asn
            20                  25                  30
Cys Tyr Asn Ser Ala Thr Leu Cys Met His Ala Asn Thr His Tyr Trp
        35                  40                  45
Thr Gly Lys Met Ile Asn Pro Ser Cys Pro Gly Gly Leu Gly Ala Thr
    50                  55                  60
Val Cys Trp Thr Tyr Phe Thr His Thr Ser Met Ser Asp Gly Gly Gly
65                  70                  75                  80
Ile Gln Gly Gln Ala Arg Glu Lys Gln Val Lys Glu Ala Ile Ser Gln
                85                  90                  95
Leu Thr Arg Gly His Ser Thr Pro Ser Pro Tyr Lys Gly Leu Val Leu
            100                 105                 110
Ser Lys Leu His Glu Thr Leu Arg Thr His Thr Arg Leu Val Ser Leu
        115                 120                 125
Phe Asn Thr Thr Leu Thr Arg Leu His Glu Val Ser Ala Gln Asn Pro
    130                 135                 140
Thr Asn Cys Trp Met Cys Leu Pro Leu His Phe Arg Pro Tyr Ile Ser
145                 150                 155                 160
Ile Pro Val Pro Glu Gln Trp Asn Asn Phe Ser Thr Glu Ile Asn Thr
                165                 170                 175
Thr Ser Val Leu Val Gly Pro Leu Val Ser Asn Leu Glu Ile Thr His
            180                 185                 190
Thr Ser Asn Leu Thr Cys Val Lys Phe Ser Asn Thr Ile Asp Thr Thr
        195                 200                 205
Ser Ser Gln Cys Ile Arg Trp Val Thr Pro Pro Thr Arg Ile Val Cys
    210                 215                 220
Leu Pro Ser Gly Ile Phe Phe Val Cys Gly Thr Ser Ala Tyr His Cys
225                 230                 235                 240
Leu Asn Gly Ser Ser Glu Ser Met Cys Phe Leu Ser Phe Leu Val Pro
                245                 250                 255
Pro Met Thr Ile Tyr Thr Glu Gln Asp Leu Tyr Asn His Val Val Pro
            260                 265                 270
Lys Pro His Asn Lys Arg Val Pro Ile Leu Pro Phe Val Ile Arg Ala
        275                 280                 285
Gly Val Leu Gly Arg Leu Gly Thr Gly Ile Gly Ser Ile Thr Thr Ser
    290                 295                 300
Thr Gln Phe Tyr Tyr Lys Leu Ser Gln Glu Ile Asn Gly Asp Met Glu
305                 310                 315                 320
Gln Val Thr Asp Ser Leu Val Thr Leu Gln Asp Gln Leu Asn Ser Leu
                325                 330                 335
Ala Ala Val Val Leu Gln Asn Arg Arg Ala Leu Asp Leu Leu Thr Ala
            340                 345                 350
Lys Arg Gly Gly Thr Cys Leu Phe Leu Gly Glu Glu Arg Cys Tyr Tyr
        355                 360                 365
Val Asn Gln Ser Arg Ile Val Thr Glu Lys Val Lys Glu Ile Arg Asp
    370                 375                 380
Arg Ile Gln Cys Arg Ala Glu Glu Leu Gln Asn Thr Glu Arg Trp Gly
385                 390                 395                 400
Leu Leu Ser Gln Trp Met Pro Trp Val Leu Pro Phe Leu Gly Pro Leu
                405                 410                 415
```

-continued

```
Ala Ala Leu Ile Leu Leu Leu Leu Phe Gly Pro Cys Ile Phe Asn Leu
        420             425             430

Leu Val Lys Phe Val Ser Ser Arg Ile Glu Ala Val Lys Leu Gln Met
        435             440             445

Val Leu Gln Met Glu Pro Gln Met Glu Ser Met Thr Lys Ile His Arg
    450             455             460

Gly Pro Leu Asp Arg Pro Ala Ser Pro Cys Ser Asp Val Asn Asp Ile
465             470             475             480

Glu Gly Thr Pro Pro Glu Glu Ile Ser Thr Ala Gln Pro Leu Leu Cys
            485             490             495

Pro Asn Ser Ala Gly Ser Ser
            500
```

LTR REGION OF MSRV-1 AND THE PROTEINS IT ENCODES, AND PROBES AND METHODS FOR DETECTING MSRV-1 RETROVIRUS

This is a Continuation of Application No. 09/890,340, now abandoned, which is a U.S. National Stage Application of PCT/IB00/00159, filed Feb. 15, 2000. The entire disclosure of the prior applications is hereby incorporated by reference herein in its entirety.

Multiple sclerosis (MS) is a demyelinating disease of the central nervous system (CNS) the cause of which remains as yet unknown.

Many studies have supported the hypothesis of a viral aetiology of the disease, but none of the known viruses tested has proved to be the causal agent sought: a review of the viruses sought for several years in MS has been compiled by E. Norrby and R. T. Johnson.

Recently, a retrovirus different from the known human retroviruses has been isolated in patients suffering from MS. The authors were also able to show that this retrovirus could be transmitted in vitro, that patients suffering from MS produced antibodies capable of recognizing proteins associated with the infection of leptomeningeal cells by this retrovirus, and that the expression of the latter could be strongly stimulated by the immediate-early genes of some herpesviruses.

All these results point to the role in MS of at least one unknown retrovirus or of a virus having reverse transcriptase activity which is detectable according to the method published by H. Perron and qualified as "LM7-like RT" activity.

The Applicant's studies have enabled two continuous cell lines infected with natural isolates originating from two different patients suffering from MS to be obtained by a culture method as described in U.S. Pat. No. 5,650,318, the content of which is incorporated in the present description by reference. These two lines, derived from human choroid plexus cells, designated PLI-2 and LM7PC, were deposited with the ECACC on 22nd July 1992 and 8th January 1993, respectively, under numbers 92072201 and 93010817, in accordance with the provisions of the Budapest Treaty. Moreover, the viral isolates possessing LM7-like RT activity were also deposited with the ECACC under the overall designation of "strains". The "strain" or isolate harboured by the PLI-2 line, designated POL-2, was deposited with the ECACC on 22nd July 1992 under No. V92072202. The "strain" or isolate harboured by the LM7PC line, designated MS7PG, was deposited with the ECACC on 8th January 1993 under No. V93010816.

Starting from the cultures and isolates mentioned above, characterized by biological and morphological criteria, the next step was to endeavour to characterize the nucleic acid material associated with the viral particles produced in these cultures.

The portions of the genome which have already been characterized have been used to develop tests for molecular detection of the viral genome and immunoserological tests, using the amino acid sequences encoded by the nucleotide sequences of the viral genome, in order to detect the immune response directed against epitopes associated with the infection and/or viral expression.

The viral system discovered by the Applicant is related to a complex retroviral system. In effect, the sequences to be found encapsidated in the extracellular viral particles produced by the different cultures of cells of patients suffering from MS show clearly that there is coencapsidation of retroviral genomes which are related but different from the "wild-type" retroviral genome which produces the infective viral particles. This phenomenon has been observed between replicative retroviruses and endogenous retroviruses belonging to the same family, or even heterologous retroviruses. The notion of endogenous retroviruses is very important. In the case of MSRV-1, it has been observed that endogenous retroviral sequences comprising sequences homologous to the MSRV-1 genome exist in normal human DNA. The existence of endogenous retroviral elements (ERV) related to MSRV-1 by all or part of their genome explains the fact that the expression of the MSRV-1 retrovirus in human cells is able to interact with closely related endogenous sequences.

Defective clones which only express proteins may be involved in the pathology.

The Applicant has made an unexpected discovery, according to which RU5 region of a retroviral LTR that is defined in the present invention, encodes the expression of at least one protein. This is unusual for LTRs, in particular in the RU5 region.

The present invention first relates to a nucleotide fragment of a LTR-RU5 region comprising a nucleotide sequence which encodes the expression of a protein, wherein said protein comprises at least six, preferably at least eight, and more preferably at least twelve, amino acids of a peptide sequence selected from the group consisting of SEQ ID NO:2, SEQ ID NO:3 and SEQ ID NO:4, and a complementary nucleotide fragment.

Advantageously, a nucleotide fragment of the invention, or the complementary nucleotide fragment thereof, comprises a nucleotide sequence which encodes the expression of a protein, wherein said protein comprises a peptide sequence selected from SEQ ID NO:2, SEQ ID NO:3 and SEQ ID NO:4, and complementary nucleotide fragment. Preferably said protein consists of SEQ ID NO:3 or comprises or consists of SEQ ID NO:2 and SEQ ID NO:4.

The invention also relates to the following matter:
a nucleic acid probe for the detection of MSRV-1 retrovirus, which comprises 10 to 1000 monomers and specifically hybridizes with the nucleotide fragment of the invention, in high stringency conditions;
a primer for the amplification by polymerization of a nucleic acid retroviral sequence of MSRV-1 virus, which comprises 10 to 30 monomers and hybridizes with the nucleotide fragment of the invention, in high stringency conditions
a protein encoded by a nucleotide fragment of the invention preferably, said protein comprises a peptide sequence selected from the group consisting of SEQ ID NO:2, SEQ ID NO:3 and SEQ ID NO:4, or consists of a peptide sequence selected from the group consisting of SEQ ID NO:3, SEQ ID NO:2 and SEQ ID NO:4;
a polypeptide comprising at least six, preferably at least eight, and more preferably at least twelve, amino acids of SEQ ID NO:4;
a polyclonal or monoclonal antibody directed against a protein of the invention or a polypeptide of the invention;
a process for detecting, in a biological sample, the presence of MSRV-1 retrovirus comprising:
contacting a probe of the invention with said biological sample, determining whether the probe binds to a nucleic acid in said biological sample, wherein binding indicates the presence of MSRV-1 virus; said process may comprise an amplification step wherein said nucleic acid is amplified with a primer of the invention;

a process for detecting, in a biological sample, the presence of MSRV-1 retrovirus comprising:

contacting an antibody of the invention with said biological sample, determining whether the antibody binds to a protein of the invention, in said biological sample, wherein binding indicates the presence of MSRV-1 virus;

a process for detecting, in a biological sample, the presence of MSRV-1 retrovirus comprising detecting the antigenic or biological properties of a protein of the invention or a fragment thereof; advantageously, said protein fragment is a polypeptide of the invention.

Before describing the invention in detail, different terms used in the description and the claims are now defined:

the term "MSRV" used in the present description denotes any pathogenic and/or infective agent associated with MS, in particular a viral species, the attenuated strains of the said viral species or the defective-interfering particles or particles containing coencapsidated genomes, or alternatively genomes recombined with a portion of the MSRV-1 genome, derived from this species. Viruses, and especially viruses containing RNA, are known to have a variability resulting, in particular, from relatively high rates of spontaneous mutation;

human virus is understood to mean a virus capable of infecting, or of being harboured by human beings, according to the invention, a nucleotide fragment or an oligonucleotide or polynucleotide is an arrangement of monomers, or a biopolymer, characterized by the informational sequence of the natural nucleic acids, which is capable of hybridizing with any other nucleotide fragment under predetermined conditions, it being possible for the arrangement to contain monomers of different chemical structures and to be obtained from a molecule of natural nucleic acid and/or by genetic recombination and/or by chemical synthesis; a nucleotide fragment may be identical to a genomic fragment of the MSRV-1 virus discussed in the present invention;

thus, a monomer can be a natural nucleotide of nucleic acid whose constituent elements are a sugar, a phosphate group and a nitrogenous base; in RNA the sugar is ribose, in DNA the sugar is 2-deoxyribose; depending on whether the nucleic acid is DNA or RNA, the nitrogenous base is chosen from adenine, guanine, uracil, cytosine and thymine; or the nucleotide can be modified in at least one of the three constituent elements; as an example, the modification can occur in the bases, generating modified bases such as inosine, 5-methyldeoxycytidine, deoxyuridine, 5-(dimethylamino) deoxyuridine, 2,6-diaminopurine, 5-bromodeoxyuridine and any other modified base promoting hybridization; in the sugar, the modification can consist of the replacement of at least one deoxyribose by a polyamide, and in the phosphate group, the modification can consist of its replacement by esters chosen, in particular, from diphosphate, alkyl- and arylphosphonate and phosphorothioate esters;

<<informational sequence) is understood to mean any ordered succession of monomers whose chemical nature and order in a reference direction constitute or otherwise an item of functional information of the same quality as that of the natural nucleic acids;

hybridization is understood to mean the process during which, under suitable working conditions, two nucleotide fragments having sufficiently complementary sequences pair to form a complex structure, in particular double or triple, preferably in the form of a helix in particular in high stringency conditions (see Maniatis et al., Molecular Cloning, Cold Spring Harbor, 1982); in general, depending on the length of the probes used, these conditions are the following: the temperature for the hybridization reaction is between approximately 20° C. and 65° C., and especially between 35° C. and 65° C., in a saline solution at a concentration of approximately 0.8 to 1 M;

a probe comprises a nucleotide fragment synthesized chemically or obtained by digestion or enzymatic cleavage of a longer nucleotide fragment, comprising at least six monomers, advantageously from 10 to 100 monomers and preferably 10 to 30 monomers, and possessing a specificity of hybridization under high stringency conditions; preferably, a probe possessing fewer than 10 monomers is not used alone, but is used in the presence of other probes of equally short size or otherwise; under certain special conditions, it may be useful to use probes of size greater than 100 monomers; a probe may be used, in particular, for diagnostic purposes, such molecules being, for example, capture and/or detection probes;

the capture probe may be immobilized on a solid support by any suitable means, that is to say directly or indirectly, for example by covalent bonding or passive adsorption the detection probe may be labelled by means of a label chosen, in particular, from radioactive isotopes, enzymes chosen, in particular, from peroxidase and alkaline phosphatase and those capable of hydrolysing a chromogenic, fluorogenic or luminescent substrate., chromophoric chemical compounds, chromogenic, fluorogenic or luminescent compounds, nucleotide base analogues and biotin;

the probes used for diagnostic purposes of the invention may be employed in all known hybridization techniques, and in particular the techniques termed <<DOT-BLOT>>, <<SOUTHERN BLOT>>, <<NORTHERN BLOT>>, which is a technique identical to the <<SOUTHERN BLOT>> technique but which uses RNA as target, and the SANDWICH technique; advantageously, the SANDWICH technique is used in the present invention, comprising a specific capture probe and/or a specific detection probe, on the understanding that the capture probe and the detection probe must possess an at least partially different nucleotide sequence, a primer is a probe comprising at least six monomers, and advantageously from 10 to 30 monomers, possessing a specificity of hybridization under high stringency conditions for the initiation of an enzymatic polymerization, for example in an amplification technique such as PCR (polymerase chain reaction), in an elongation process such as sequencing, in a method of reverse transcription or the like;

In view of the fact that a virus possessing reverse transcriptase enzymatic activity may be genetically characterized equally well in RNA and in DNA form, both the viral DNA and RNA will be referred to for characterizing the sequences relating to a virus possessing such reverse transcriptase activity, termed MSRV-1 according to the present description.

Detection of a substance or agent is understood below to mean both an identification and a quantification, or a separation or isolation, of the said substance or said agent.

A better understanding of the invention will be gained on reading the detailed description which follows, prepared with reference to the attached figures, in which:

FIG. 1 shows the 5' nucleotide sequence of the RU5 region obtained from clone LB15 nucleotides 1 to 623 of SEQ ID NO:14) and the 5' gag region obtained from clones CL2 (nucleotides 624 to 1680 of SEQ ID NO:14) and CL17 nucleotides 1681 to 2052 of SEQ IID NO:14). The amino acid (AA) translation is shown under the gag nucleotide sequence (SEQ ID NOS:15-17, wherein AA 1-420 are found in SEQ ID NO:15, AA 422-469 are found in SEQ ID NO:16, and AA 471-486 are found in SEQ ID NO:17). The polyadenylation site in R is boxed and the polyadenylation downstream signal in U5 is underlined. (II) indicates a frameshift and (.) represents a stop codon. Amino acid positions in bold correspond to the major homology region (MHR) in the sequence encoding the capsid. Underlined amino acid positions correspond to the conserved positions in the sequence encoding the nucleocapsid.

Figure 2:
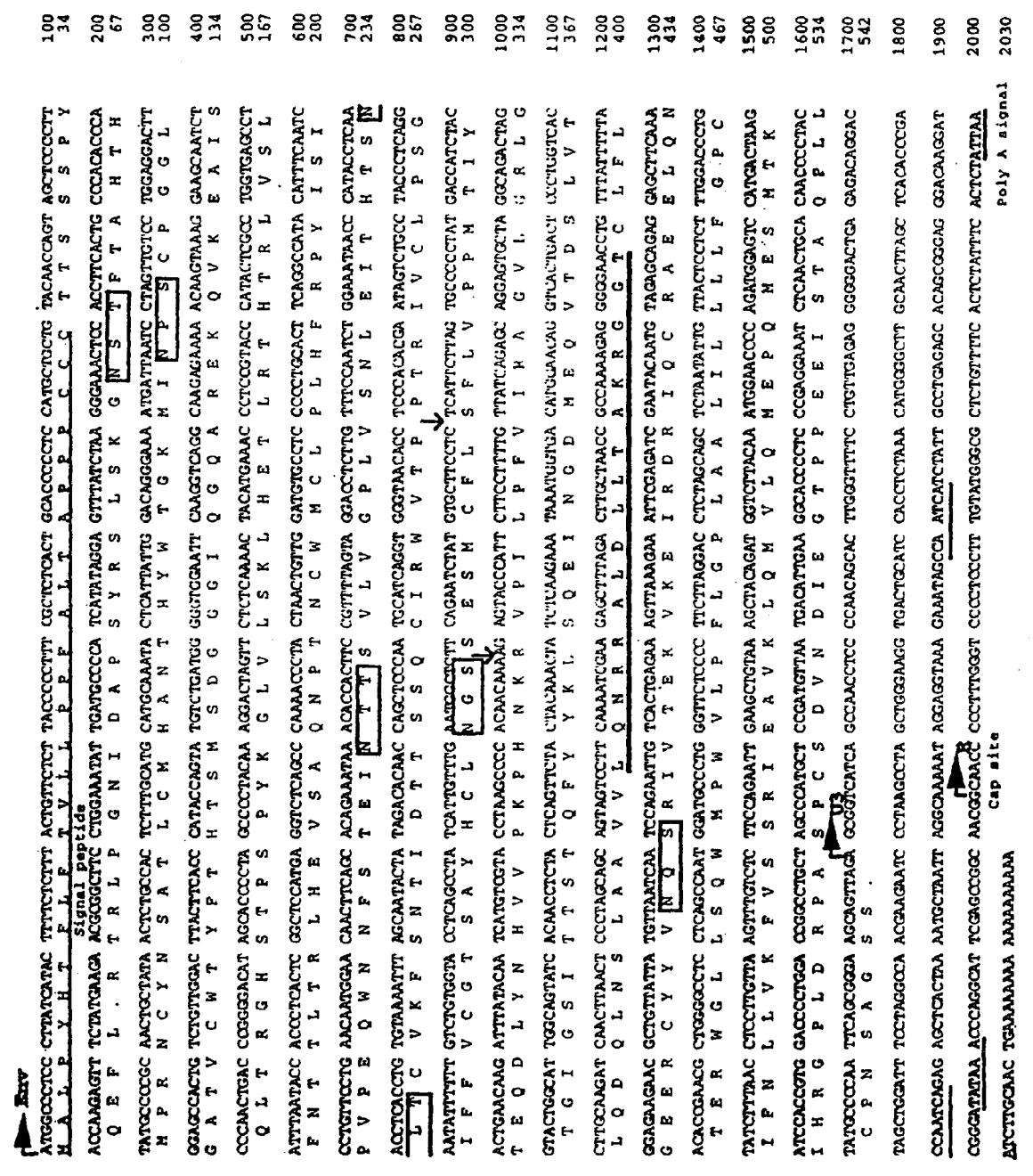

FIG. 2 shows the 5' env region obtained from clone C15 (nucleotides 1 to 1479 of SEQ ID NO:18) and the 3' env and LTR sequences obtained from clone CL6 (nucleotides 1480 to 2030 of) (SEQ ID NO:18). The amino acid (AA) translation is shown under the env nucleotide sequence (SEQ ID NOS:19 and 20, wherein AA 1-38 are found in SEQ ID NO:19 and AA 39-542 are found in SEQ ID NO:20). Horizontal arrows indicate the env region and the U3, and R substructures. In the env region, the signal peptide and the putative immunosuppressive peptide are underlined, the N-linked glycosylation sites are boxed, and the two putative cleavage sites are indicated by vertical arrows. In the U3R region; the CAAT regulatory element, the polyA signal, and the TATA box are underlined, and the cap site is indicated.

Figure 3:
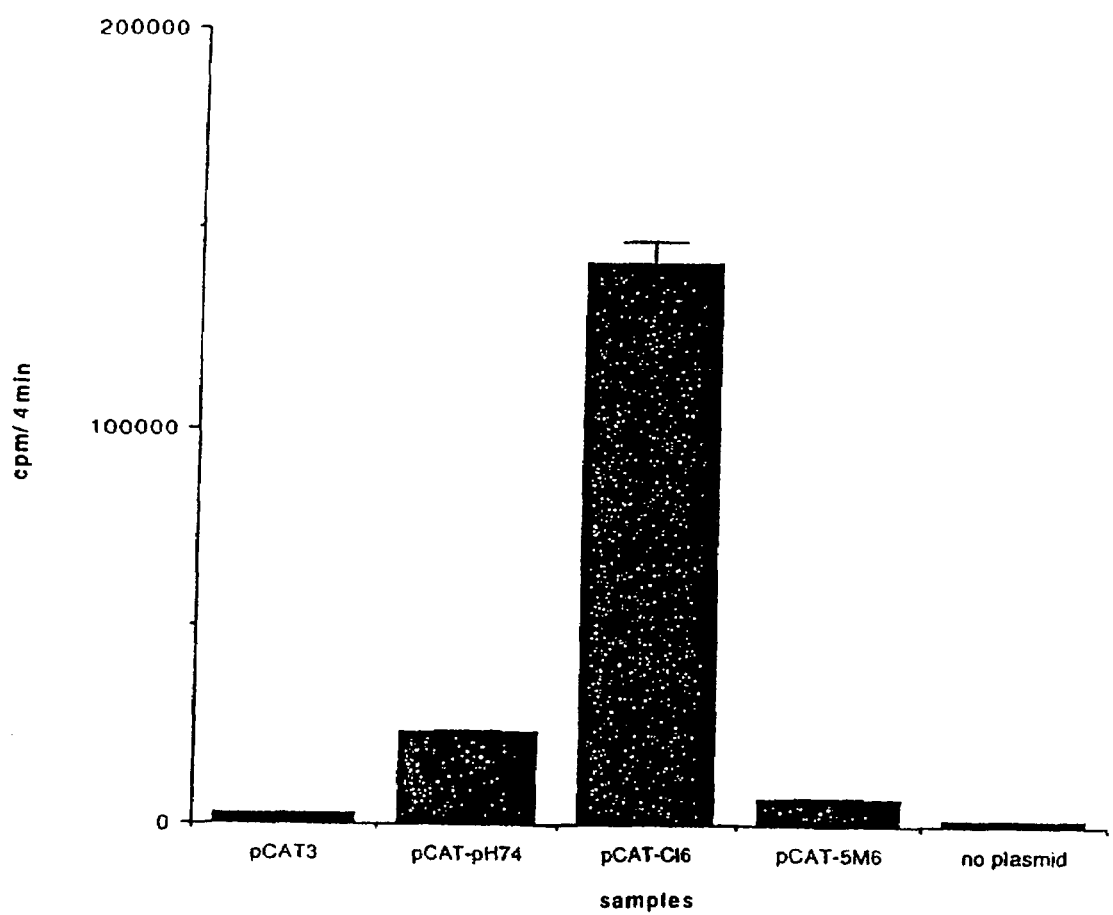

FIG. 3 is a graph of the promoter activity of U3R clones obtained from MS plasma RNA (CL6), normal placenta RNA (PH74, accession number AF072506) and human cell DNA (5M6). U3R sequences were cloned into the pCAT3 Enhancerr reporter vector. CAT activity, evaluated after 48 hours of incubation, represents the promoter efficiency of the corresponding sequences. The values presented correspond to the mean of 3 independent experiments.

EXAMPLE 1:

Determination of MSRV-LTR regions

A RT-PCR amplification was performed with antisense 3' primers located in the gag region and a 5' sense primer defined from the R sequence previously obtained in the 3' end (clone 6, described below). The clone LB15 (SEQ ID NO:1), encompassing R (87 bp), U5 (456 bp), PBS, and 5' gag regions, was thus obtained from concentrated culture particles. A polyadenylation site is compatible with the "CA" dinucleotide motif located at the junction of R and U5 regions and a putative poly(A) downstream signal is located at a distance of 24 nucleotides downstream of the poly(A) signal, with the consensus sequence "YGTGTTYY" (SEQ ID NO:5). The putative primer-binding site (PBS), identified downstream of the U5 region, has proved to be related to the 3' end of the avian tRNA$^{Trp}$ complementary sequence.

It is also noteworthy that 2 rather short in-frame orfs (SEQ ID NO:2 and SEQ ID NO:3 were found in the RU5 region. The 3' LTR U3R region was identified in the CL6 clone (FIG. 2) obtained by amplification on DNase-treated RNA extracted from MS plasma. By comparison with the 5' LTR sequences obtained by 5' extension on MSRV RNA, a 299 bp-long U3 region and a 84 bp-long R region in CL6 LTR region, located downstream the env orf and ending with the polyA-tail has been identified. The typical regulatory element CAAT box was observed in two locations in the putative U3 region, but other putative binding sites for several transcription factors were also detected with Transcription Factor database (Heinemeyer T, Wingender, E, Reuter, I, Hermjakob, H, Kel, A E, Kel, O V, Ignatieva, E V, Ananko, E A, Podkolodnaya, O A, Kolpakov, F A, Podkolodny, N L, and Kolchanov, N A. (1998). Databases on transcriptional regulation: TRANSFAC, TRRD, and COMPEL. *Nucleic Acids Res*. 26, 364-370).

A TATA box (TATAAA) was observed in the U3 region as described for numerous retroviruses. Finally, a poly(A) signal (AATAAA) was found 83 bp downstream of the TATA box.

In order to evaluate the promotor activity of LTR clones from different origins, CAT assays with sub-cloned U3R regions from LTR clones obtained from MS plasma RNA (CL6) and from related HERV-W copies in non-MS DNA (5M6) and in non-MS placenta RNA (PH74) were performed. As shown in FIG. 3, a potent activity was associated with the LTR sequence in CL6 clone from MS plasma, whereas a weak and moderate promotor activity was found with 5M6 and PH74 clones respectively. Similar results were obtained with different cell types.

EXAMPLE 2

Material and Methods Used in Example 1

Total RNA was extracted from MS plasma or purified particles by standard acidified guanidium thiocyanate procedure or by the <<viral RNA extraction kit>> (Boehringer Mannheim). After a DNase I treatment, RNA was reverse transcribed (Expand™ RT, Boehringer Mannheim) with either random hexanucleotide primers, specific MSRV primer or anchored oligodT primer, and was amplified by nested or semi-nested PCR (Long Expand PCR kit—Boerhinger Mannheim). For each assay, a no-RT control was performed 5' and 3' extension from the MSRV pol region was performed to obtain clones with primers indicated below.

LB15:
Sense primer (SEQ ID NO:8)
5'GCAACAGCAACCCCCTTTGGGT 3'

Antisense primers (SEQ ID NO:9)
5'CTTGGAGGGTGCATAACCAGGGAAT 3'

(SEQ ID NO:10)
5'CTATGTCCTTTTGGACTGCTGTTTGGGT 3'

CL6:
Sense primers (SEQ ID NO:11)
5'GCCATCAAGCCACCCAAGAACTCTTAACTT 3'

(SEQ ID NO:12)
5'CCAATAGCCAGACCATTATATACACTAATT 3'

Antisense primer (SEQ ID NO:13)
5'GACTCGCTGCAGATCGATTTTTTTTTTTTTTTT 3'

PCR fragments were cloned into a pCR2.1 of the TA cloning™ kit (Invitrogen) and were sequenced in the both directions using the 'Prism ready reaction kit dye deoxyterminator cycle sequencing kit' (Applied Biosystems), with the Applied Biosystem 377 and 373A automated DNA sequencers.

U3R regions from CL6 (as shown in WO-99/02666 in the name of Applicant), PH74 (as shown in WO-99/02696 in the name of Applicant) and 5M6 (as shown in WO-99/02666 in the name of Applicant) clones (respectively obtained from MS plasma RNA, placenta RNA and Human DNA), were cloned into pCAT3 (Promega-Biotech, Madison, Wis., USA) for CAT assays. Transfection experiments were performed on Hela, PG4, BeWo or Jurkat cells using the Superfect Transfection Kit (Qiagen GmbH, Germany) with 2 μg of purified recombinant plasmid. After 48 h of incubation, the cells were harvested in order to evaluate CAT activity by the use of the CAT Enzyme Assay System (Promega-Biotech). For this purpose the Liquid Scintillation Counting (LSC) protocol was followed as recommended by the manufacturer. A positive control consisted of cells transfected by 2 μg of pCAT3 Contol' (Promega-Biotech).

The invention claimed is:

1. An isolated nucleotide fragment comprising a nucleotide sequence that encodes a protein having a sequence comprising SEQ ID NO: 2, wherein the encoding nucleotide sequence is located in the RU5 region of MSRV-1.

2. The nucleotide fragment of claim 1, wherein said protein has a sequence comprising SEQ IID NO: 2.

3. The isolated nucleotide fragment of claim 1, wherein said protein has a sequence comprising SEQ ID NO: 4.

4. The isolated nucleotide fragment of claim 1, wherein said protein has a sequence consisting of SEQ ID NO: 2 or SEQ ID NO: 4.

* * * * *